(12) United States Patent
Kato

(10) Patent No.: US 7,564,944 B2
(45) Date of Patent: Jul. 21, 2009

(54) METHOD FOR INSPECTING CERAMIC STRUCTURES

(75) Inventor: Shigeki Kato, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 326 days.

(21) Appl. No.: 10/592,442

(22) PCT Filed: Mar. 31, 2005

(86) PCT No.: PCT/JP2005/006817
§ 371 (c)(1),
(2), (4) Date: Sep. 11, 2006

(87) PCT Pub. No.: WO2005/095932
PCT Pub. Date: Oct. 13, 2005

(65) Prior Publication Data
US 2008/0205596 A1     Aug. 28, 2008

(30) Foreign Application Priority Data
Mar. 31, 2004    (JP)    ............... 2004-102320

(51) Int. Cl.
G01N 23/02    (2006.01)
G01N 23/00    (2006.01)
(52) U.S. Cl. .......................................... 378/58; 378/27
(58) Field of Classification Search ............... 378/4, 378/5, 19, 57, 58, 62, 70–77
See application file for complete search history.

(56) References Cited
U.S. PATENT DOCUMENTS
4,601,050 A * 7/1986 Tanaka ..................... 378/18

5,430,291 A   7/1995  Pepin et al.
2003/0182930 A1  10/2003  Goulette et al.

(Continued)

FOREIGN PATENT DOCUMENTS
EP    1 389 444 A1    2/2004

(Continued)

OTHER PUBLICATIONS

Lu, Peizhen et al., "X-ray Computed Tomography and Mercury Porosimetry for Evaluation of Density Evolution and Porosity Distribution," J Am. Ceram. Soc., Journal of the American Ceramic Society, vol. 83, No. 3, pp. 518-522, XP-002334965 (2000).

(Continued)

*Primary Examiner*—Ed Glick
*Assistant Examiner*—Irakli Kiknadze
(74) *Attorney, Agent, or Firm*—Oliff & Berridge, PLC

(57) ABSTRACT

There is provided a nondestructive method for inspecting ceramic structures, the method which not only easily detects the position and size of an internal defect in a ceramic structure in a short time, but also accurately identifies the position, shape, and size of the internal defect. In the method, the distribution of X-ray absorption coefficients (CT numbers) at fault planes of the ceramic structure is measured by irradiating the periphery of the ceramic structure with X rays along the periphery of the ceramic structure so that the X rays scan the entire periphery. The X rays are emitted from an X-ray tube at a tube voltage in the range of 80 to 400 kV and a tube current in the range of 2 to 400 mA.

6 Claims, 2 Drawing Sheets

U.S. PATENT DOCUMENTS

2004/0032928 A1    2/2004    Toth et al.

FOREIGN PATENT DOCUMENTS

| JP | A-61-14550 | 1/1986 |
|---|---|---|
| JP | A-63-203137 | 8/1988 |
| JP | A 2000-193582 | 7/2000 |
| JP | A-2001-201465 | 7/2001 |
| WO | WO 02/082035 A1 | 10/2002 |

OTHER PUBLICATIONS

Mucke, U et al., "The Investigation of Porosity Distribution in a SiC-ceramic Using 3D X-ray Tomography and Optical Light Microscopy," The Inst. of Elec. Engineers, vol. 35, No. 12, Abstract, XP-002335328 (1998).

Mitsukuni Mizuno et al, *Estimation of Internal Packing Characteristics of Ultrafine Particle Bed by X-Ray Computed Tomography Method*, Department of Chemical Engineering, Nagoya University, Nagoya, 464-01; English abstract on p. 394, (Jan. 17, 1991).

* cited by examiner

METHOD FOR INSPECTING CERAMIC STRUCTURES

TECHNICAL FIELD

The present invention relates to a method for inspecting ceramic structures in which the distribution of X-ray absorption coefficients (CT numbers) at the fault planes of a ceramic structure is measured by irradiating the ceramic structure with X rays along the periphery of the ceramic structure so that the x rays scan the entire periphery, and particularly to an inspection method using high density resolution X-ray computed tomography (CT).

BACKGROUND ART

Ceramic structures (for example, honeycomb structures) are often used for filters and catalyst carriers, for example, in exhaust gas purifying systems of heat engines, such as internal combustion engines, and combustion equipment, such as boilers, in liquid or gaseous fuel reformers, and in water and sewage purifying systems. In particular, ceramic structures are suitably used in diesel particulate filters (hereinafter referred to as DPFs) or high-temperature gas dust collector for collecting and removing particulate matter from dust-containing fluid, such as exhaust gas emitted from diesel engines.

Such a ceramic structure traps and removes unnecessary particulate matters when fluid to be treated passes through the pores in porous partition wall of the structure, or the ceramic structure is allowed to carry a catalyst on the surfaces of the porous partition wall or in the pores so that the fluid is brought into contact with the catalyst.

If the ceramic structure has large holes penetrating the porous partition wall, the large holes negatively affect the filtration performance or the ability to function as a catalyst carrier of the ceramic structure, and bring about defects. It is therefore important to detect such large holes. It is also important to examine the size and number of the holes penetrating the partition wall, in estimating the ability if the ceramic structure is used as a filter or the like.

In order to inspect filters having such a structure for a defect, a method using powder having a specific particle size has been proposed in, for example, Japanese Unexamined Patent Application Publication No. 2000-193582. This method inspects pinholes in the partition walls by detecting the powder discharged from the filter with a particle counter. Unfortunately, the method allows the powder to remain in the filter, and the remaining powder must be removed. Also, this method is not suitable for inspecting the pore size of the filter because the powder cannot be discharged unless the filter has pinholes.

Another method (LS, light scattering) has also been proposed in, for example, PCT Publication No. WO 02/082035 for detecting a defect in a test body. In this method, fine particles are introduced into the test body and particles discharged from the test body are irradiated with laser light so that the particles are visible. This method is advantageous in identifying the position of the defect in the cross-sectional direction, but unsuitable for inspecting the shape and size of the defect.

For inspection for, particularly, an internal defect in a filter having the above structure, it has been necessary to destroy the test body or product since old days. Destructive inspection is much expensive in time and effort and less accurate. Specimens subjected to destructive inspection are not used for other inspections for evaluating the entirety of the product, such as strength, disadvantageously.

In order to overcome those disadvantages, nondestructive inspection with X rays is beginning to be applied to inspect structures for defects. For example, an industrial X-ray CT apparatus makes it possible to detect internal fractures or defects which have not been detected by conventional radioscopy and to analyze the three-dimensional structure of test bodies.

However, this method has been mainly approached from the viewpoint of increasing the voltage of the X-ray tube to enhance the spatial resolution (that is, how finely the apparatus can inspect a test body), but has not taken into account the density resolution (that is, for example, how finely the apparatus can show the difference in density among adjacent materials in a test body). Consequently, this method cannot sufficiently estimate the density of particularly ceramic structures, and thus makes unclear the boundary between the internal defect and the internal structure. Thus, it has been difficult to accurately identify the position, shape, and size of the internal defect.

DISCLOSURE OF INVENTION

Accordingly, an object of the present invention is to provide a nondestructive method for inspecting ceramic structures, the method which not only easily detects the position and size of an internal defect in a ceramic structure in a short time, but also accurately identifies the position, shape, and size of the internal defect.

In order to accomplish the object, the present invention provides a method for inspecting ceramic structures described below.

The method includes the step of measuring the distribution of X-ray CT numbers at the fault planes of a ceramic structure by irradiating the ceramic structure with X rays along the periphery of the ceramic structure so that the X rays scan the entire periphery. The X rays are emitted from an X-ray tube at a tube voltage in the range of 80 to 400 kV and a tube current in the range of 2 to 400 mA.

Preferably, the tube voltage of X-ray tube is in the range of 80 to 135 kV and the tube current of the X-ray tube is in the range of 10 to 400 mA.

More preferably, the tube voltage of the X-ray tube is in the range of 80 to 120 kV, and the tube current of the X-ray tube is in the range of 100 to 200 mA The method for inspecting ceramic structures may further include the step of determining the porosity of the ceramic structure from the measured CT numbers.

Preferably, the X rays scan the entire periphery of the ceramic structure in a helical manner.

The ceramic structure may be a honeycomb structure.

The honeycomb structure has a plurality of through-holes penetrated in the axis direction, partitioned by porous partition walls, and some of the through-holes are plugged at the ends on one side in the axis direction and the other through-holes are plugged at the ends on the other side.

The method of the present invention can easily and three-dimensionally identify the position, shape, and size of the internal defect in a ceramic structure in a nondestructive manner in a short time.

BEST MODE FOR CARRYING OUT THE INVENTION

The method for inspecting a ceramic structure will now be described in detail with reference to preferred embodiments. However, it will be readily appreciated by those skilled in the art that the invention is not limited to the embodiments, and that various modifications may be made in the invention without departing from the scope and spirit of the invention.

Figure 1:
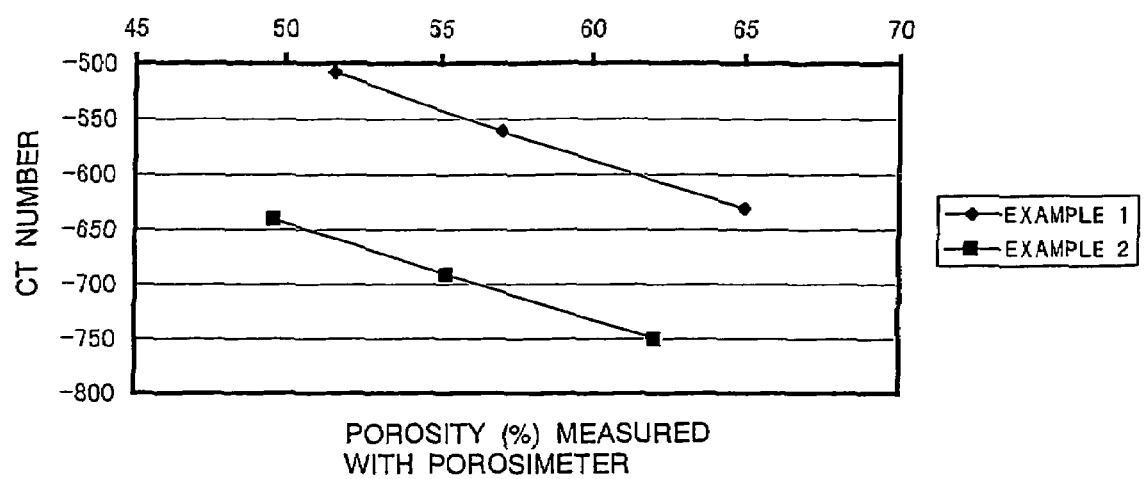
FIG. 1 is a plot showing the relationship between the porosity (%) measured with a porosimeter and the CT number of DPFs prepared in the examples.
Figure 2:
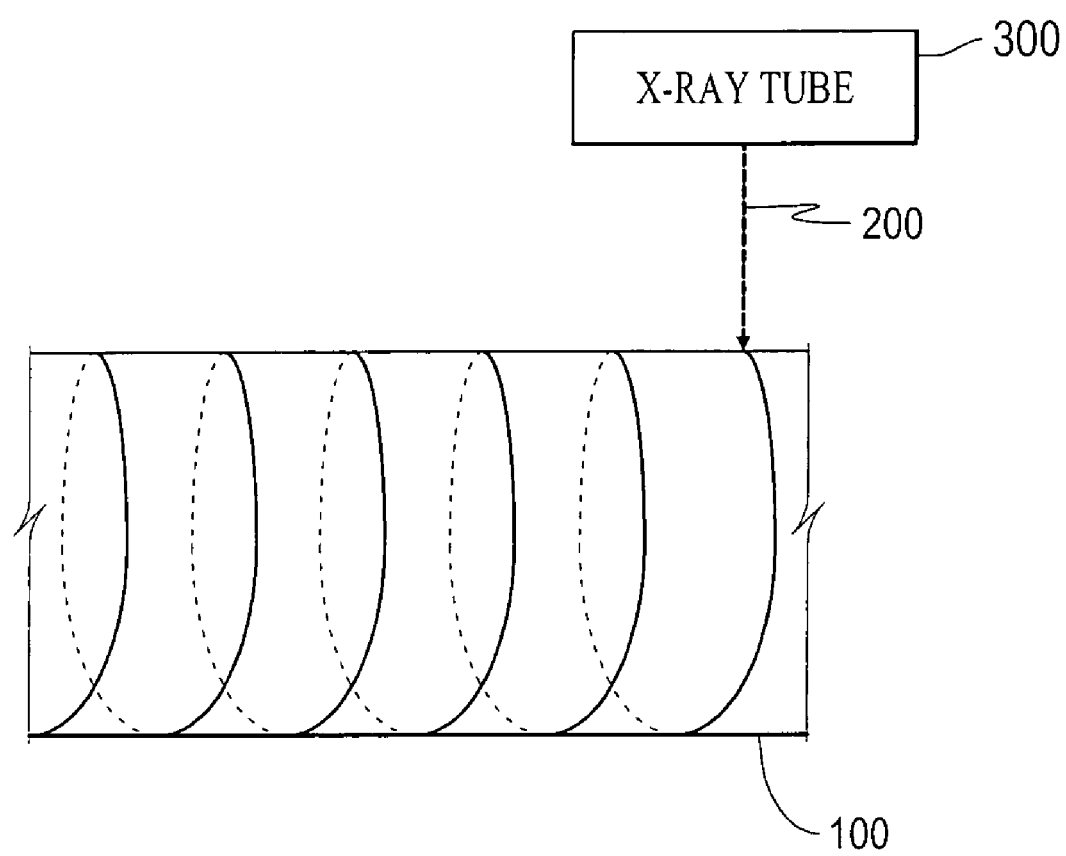
FIG. 2 shows an X-ray tube that irradiate a ceramic structure with X-rays in a helical manner.

As shown in FIG. 2, in a method for inspecting ceramic structures according to the embodiment of the present invention, the distribution of X-ray absorption coefficients (CT numbers) is measured at the fault planes of a ceramic structure 100 by irradiating the ceramic structure with X rays along the periphery of the ceramic structure so that the X rays scan the entire periphery. In this instance, the X rays 200 are emitted from an X-ray tube 300 at a voltage in the range of 80 to 400 kV and a current in the range of 2 to 400 mA.

Preferably, the voltage of the X-ray tube is in the range of 80 to 135 kV, more preferably 80 to 120 kV, and the current of the X-ray tube is in the range of 10 to 400 mA, more preferably 100 to 200 mA.

By applying X-ray CT under the above conditions advantageous in density resolution, the density of the ceramic or ceramic material in a ceramic structure can be satisfactorily evaluated in a nondestructive manner. Accordingly, the boundary between the internal defect and the internal structure are detected so clearly that the position of the internal defect can be accurately identified and that even an internal defect as small as, for example, about 1 mm can be certainly detected.

An X-ray tube voltage of more than 400 kV cannot provide density resolution sufficient to evaluate the density of the ceramic or ceramic material in a ceramic structure, and accordingly the boundary between the internal defect and the internal structure is not detected so clearly that an internal defect as small as about 1 mm cannot be detected. An X-ray tube voltage of less than 80 kV cannot provide X-ray radiation sufficient for ceramic structure to absorb X rays, and consequently results in inaccurate inspection.

In the method of the present invention, the porosity of the ceramic structure may be determined from the measured X ray absorption coefficients (CT numbers) at the fault planes of the ceramic structure obtained by irradiating the ceramic structure with X rays along the periphery so that the X rays scan the entire periphery.

It is herein important that the CT number is proportional to the porosity measured with a mercury porosimeter (see the FIGURE).

This fact leads to nondestructive direct inspection for the porosities and internal defects of products before shipping, without applying a destructive method, such as the Archimedian method or the use of a mercury porosimeter. Thus, defective products can be prevented from being shipped. The calibration curve is appropriately prepared according to the variations of the porosity, cell structure, partition wall thickness, external wall thickness, and other factors of the ceramic structure, such as a honeycomb structure.

The CT number herein refers to a value representing the average X-ray attenuation associating with pixels of a tomogram (CT section), and represents the X-ray attenuation coefficient (X-ray absorption coefficient) of a material with respect to that of water. For example, the CT number of water and air are defined as 0 and −1000, respectively, and the CT number of a material is determined so as to produce a linear relationship with specific gravities between those of water and air.

In the method of the present invention, the distribution of X ray absorption coefficients (CT numbers) at the fault planes of the ceramic structure may be measured with a helical CT or spiral CT apparatus by irradiating the ceramic structure with X rays in a helical manner along the periphery so that the X rays scan the entire periphery, as shown in FIG. 2.

Thus, the method of the present invention can scan a ceramic structure over a large area in a short time, and continuously collect data at many cross sections. The collected data is so continuous as to lead to three-dimensional positional information (3D perspective view), and to reconstruct desired fault plane images to show the three-dimensional position, shape, and size of internal defects.

The fundamental principle of X-ray CT applied to the present invention will now be described. X-ray CT measures the intensity distribution of X rays transmitted through a test body of the X rays emitted to the test body from various directions, and the distribution of ease of X-ray transmission in the test body is three-dimensionally reconstructed from the obtained data. This is different from normal radiography which forms an image directly from the intensity distribution of X rays transmitted through a test body of the X rays emitted to the test body from a single direction. X ray CT was invented in 1971. At that time, X rays were emitted in a thin beam while mechanically scanning, and calculation was based on successive approximation. Current X-ray CT uses a fan-like beam or fan beam to reduce the time of exposure, and calculation is generally based on filtered back projection alternative to successive approximation in order to process enormous volumes of data in a short time. Furthermore, in order to photograph many cross sections in a short time, a fan beam continuously scan in a helical manner (helical CT), or a conical beam (or cone beam) is used.

The ceramic structure used in the present invention is not particularly limited, and may be a honeycomb structure. For example, it may be a honeycomb structure like a DPF having a plurality of through-holes penetrated in the axis direction, partitioned by porous partition wall, and some of which are plugged with plug members at the ends on one side in the axis direction and the others are plugged at the ends on the other side. The material of the ceramic structure may be cordierite, alumina, silicon carbide, silicon nitride, or other ceramic, and may be porous.

In inspection of such honeycomb structures, the method of the present invention allows, for example, a DPF or a converter containing a large catalyst carrier to be nondestructively inspected without being destroyed, and is accordingly very convenient and rational.

The method of the present invention, using X-ray CT under conditions advantageous in density resolution can be appropriately applied to the following applications: (1) inspection of how uniformly ceramic materials are mixed; (2) detection of the density distribution of a ceramic clay to be extruded, occurrence of carcass or agglomeration resulting from insufficient compression of the materials during screw rotation; (3) detection of loss of continuous ribs, cracks at 45° intersections of ribs, and internal defects of 0.5 mm or more in honeycomb formed bodies, honeycomb fired bodies, and DPFs, and determination of density (or porosity) and distribution of catalyst concentration from the CT number; (4) inspection for variation in depth of plug portions in DPFs; (5) detection of internal defects in melted portions of DPFs in practical use, and detection of ash or particles of unburned oil or fuel additives and determination of their distribution; and (6) detection of porosity failure in the stage of a ceramic clay, according to a measured CT number of the ceramic clay and a porosity of the fired body estimated from a calibration curve previously prepared by measuring the CT numbers of the clay, formed body, and fired body prepared from the same raw material.

EXAMPLES

The present invention will now be further described in detail with reference to examples. However, the invention is not limited to the scope of the examples.

Examples 1 and 2

(1) Preparation of Honeycomb Structure

Powder compositions of cordierite were compounded so that the porosities would be 50%, 60%, and 65% after firing. A binder and water were added to the compositions, and the mixtures were kneaded and plugged to prepare three pieces of clay. Then, each of the three pieces of clay was formed and dried to yield a dried honeycomb body. In this process, Example 1 used an extrusion die having rectangular cells with a cell density of 300 cells/in$^2$, a rib thickness of 12 mills, and an open frontal area of 62.8%, and Example 2 used an extrusion die having rectangular cells with a cell density of 100 cells/in$^2$, a rib thickness of 17 mills, and an open frontal area of 68.9%. Both ends of the dried body were cut off to form flat and smooth surfaces. The resulting body was coated with a film and provided with holes in a checkered pattern with a laser. Then, a slurry of a cordierite composition was prepared and press-fitted into the honeycomb carrier to plug the holes. The honeycomb carrier was fired at 1430° C. for 5 hours to yield a DPF (fired sample) of 160 mm in diameter by 200 mm in length. In the description, the unit in, or inch, is 2.54 cm in SI Units; the unit mill is about 0.0254 mm in SI Units.

(2) Density Measurement

The six fired samples were subjected to helical scan to be photographed under the conditions of a tube voltage of 120 kV, a tube current of 200 mA, an exposure time of 0.5 seconds per rotation, and a slice thickness of 0.5 mm with a medical X-ray CT apparatus manufactured by Toshiba Medical Systems Corporation. The density of each sample was extremely uniform, and the CT number, which indicates the density, was hardly varied. The table shows average CT numbers. Then, the sample subjected to the X-ray CT was cut, and the porosity of the sample was measured with a mercury porosimeter manufactured by Shimadzu Corporation. The results are shown in the Table and plotted in the FIGURE.

TABLE

|  | Porosity (%) | X-ray CT number |
|---|---|---|
| Example 1 | 51.5 | −508 |
|  | 57.0 | −561 |
|  | 65.0 | −631 |
| Example 2 | 49.6 | −638 |
|  | 55.2 | −691 |
|  | 62.1 | −750 |

(3) Evaluation

The porosity measured with the mercury porosimeter manufactured by Shimadzu Corporation has a strong correlation with the X-ray CT number being an indicator of the density, as shown in the FIGURE, and consequently the porosities of the DPFs were able to be measured by X-ray CT. It has also been found that the density has a relationship with the open frontal area to the cell structure, and that a high open frontal area comes to a low density.

INDUSTRIAL APPLICABILITY

The method of the present invention, using X-ray CT under conditions advantageous in density resolution can be appropriately applied to the following applications: (1) inspection of how uniformly ceramic materials are mixed; (2) detection of the density distribution of a ceramic green body to be extruded, occurrence of carcass or agglomeration resulting from insufficient compression of the materials during screw rotation; (3) detection of loss of continuous ribs, cracks at 45° intersections of ribs, and internal defects of 0.5 mm or more in honeycomb compacts, fired honeycomb bodies, and DPFs, and determination of density (or porosity) and distribution of catalyst concentration from the CT number; (4) inspection for variation in depth of hole covers in DPFs; (5) detection of internal defects in melted portions of DPFs in practical use, and detection of ash or particles of unburned oil or fuel additives and determination of their distribution; and (6) detection of porosity failure in the stage of a ceramic green body, according to a measured CT number of the ceramic green body and a porosity of the fired body estimated from a calibration curve previously prepared by measuring the CT numbers of the green body, compact, and fired body prepared from the same raw material.

The invention claimed is:

1. A method for inspecting ceramic structures, comprising the step of:
   measuring the distribution of X-ray CT numbers at fault planes of a ceramic structure by irradiating the ceramic structure with X rays along the periphery of the ceramic structure so that the X rays scan the entire periphery in a helical manner,
   wherein the X rays are emitted from an X ray tube at a tube voltage in the range of 80 to 400 kV and a tube current in the range of 2 to 400 mA.

2. The method according to claim 1, wherein the tube voltage of the X-ray tube is in the range of 80 to 135 kV, and the tube current of the X-ray tube is in the range of 10 to 400 mA.

3. The method according to claim 1, wherein the tube voltage of the X-ray tube is in the range of 80 to 120 kV, and the tube current of the X-ray tube is in the range of 100 to 200 mA.

4. The method according to claim 1, further comprising the step of determining the porosity of the ceramic structure from the measured CT numbers.

5. The method according to claim 1, wherein the ceramic structure is a honeycomb structure.

6. The method according to claim 5, wherein the honeycomb structure has a plurality of through-holes penetrated in an axis direction, partitioned by porous partition walls, and some of the through-holes are plugged at the ends on one side in the axis direction and the other through-holes are plugged at the ends on the other side.

* * * * *